United States Patent
Wilson et al.

(10) Patent No.: US 6,720,466 B2
(45) Date of Patent: *Apr. 13, 2004

(54) 1,1,1,3,3-PENTACHLOROPROPANE PROCESS PURGE STREAM CONCENTRATION USING A SECONDARY REFLUXED EVAPORATOR AND SECONDARY PRODUCT RECOVERY

(75) Inventors: Richard L. Wilson, Mulvane, KS (US); John L. Dawkins, Derby, KS (US); Rodney L. Klausmeyer, Wichita, KS (US); James J. Weller, Mulvane, KS (US)

(73) Assignee: Vulcan Chemicals Division of Vulcan Materials Company, Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/125,141

(22) Filed: Apr. 17, 2002

(65) Prior Publication Data

US 2003/0199716 A1 Oct. 23, 2003

(51) Int. Cl.$^7$ .......................... C07C 17/26; C07C 17/30; C07C 17/32; C07C 19/00; C07C 17/266; C07C 21/18

(52) U.S. Cl. ........................................ 570/257; 570/172

(58) Field of Search ................................. 570/257, 172

(56) References Cited

U.S. PATENT DOCUMENTS

| | | | | |
|---|---|---|---|---|
| 5,902,914 A | 5/1999 | Rygas et al. | ................. | 570/257 |
| 6,187,978 B1 | 2/2001 | Rygas et al. | ................. | 570/257 |
| 6,313,360 B1 | 11/2001 | Wilson et al. | ............... | 570/257 |

*Primary Examiner*—Johann Richter
*Assistant Examiner*—Elvis O. Price
(74) *Attorney, Agent, or Firm*—Armstrong, Kratz, Quintos, Hanson & Brooks, LLP.

(57) ABSTRACT

A process for economically producing 1,1,1,3,3-pentachloropropane under conditions which preserve the activity of the catalyst. In a preferred embodiment, a two-stage distillation process is employed. In the two-stage process, the size of the equipment, temperature and vacuum are varied.

18 Claims, 2 Drawing Sheets

1,1,1,3,3-PENTACHLOROPROPANE PROCESS PURGE STREAM CONCENTRATION USING A SECONDARY REFLUXED EVAPORATOR AND SECONDARY PRODUCT RECOVERY

FIELD OF THE INVENTION

The invention finds applicability in 1,1,1,3,3-pentachloropropane production.

BACKGROUND OF THE INVENTION

There is a need in industry to produce halohydrocarbons that are environmentally safe as a replacement for certain halogenated chemicals that deplete the ozone layer.

Prior Art 1,1,1,3,3-Pentachloropropane (HCC240f) can be obtained by the addition reaction of carbon tetrachloride and vinyl chloride. For example, Kotora et.al. (Journal of Molecular Catalysis, Vol.77, 51–60 (1992)) added carbon tetrachloride to vinyl chloride in a batch reaction using either cuprous chloride or tetrakis(acetonitrile)copper(I) perchlorate catalyst and n-butylamine as co-catalyst. They obtained about a 97–98% yield by these methods. Zil'berman et.al. (J.Org.Chem.USSR (Engl.Transl.), Vol. 3, 2101–2105 (1967) CAS [68(10):40147p]) used a ferrous chloride hydrate catalyst with isopropanol solvent to make a product mixture containing only 81 wt % HCC240f, together with several higher molecular weight telomers. Both of these batch methods involved aqueous wash steps for the product purification. Neither method is adaptable to a continuous process in which the catalyst is to be recycled.

Rygas et.al. (U.S. Pat. No. 5,902,914, May 11, 1999) described a continuous process for the production of haloalkanes, including HCC240f, which includes catalyst recycle and purification steps. For example, carbon tetrachloride and vinyl chloride are (A) reacted in the presence of a catalyst and a cocatalyst to produce a haloalkane product stream. This stream is (B) flash-distilled" to produce a first stream comprising unreacted feed material and the cocatalyst and a second stream containing a haloalkane product and the catalyst. The second stream from (B) is then (C) filtered to remove the catalyst, and the filtrate is (D) distilled to purify the haloalkane product. Step (D) may be carried out in the presence of metal chelating agents, such as tributylphosphate, which may act to improve the distillation yield. Their preferred catalyst/cocatalyst systems were cuprous chloride/tert-butylamine or iron powder/hexamethylphosphoramide.

However, this scheme will not work for the catalyst system described herein. In our invention, the catalyst is ferrous chloride (produced in situ from the reaction of ferric chloride and iron metal), and the cocatalyst is tributylphosphate. Tributylphosphate, being a very high-boiling substance, will not go overhead in a flash distillation such as step (B) of Rygas et.al. Further, a filtration step such as step (C) is of no value for our system, since the catalyst components ferrous chloride and ferric chloride are soluble in the reactor effluent, and even more soluble in the bottoms stream from an initial distillation step.

Rygas et.al. (U.S. Pat. No. 6,187,978 Feb. 13, 2001) have also described another process for the production of haloalkanes. For example, they disclose a process in which carbon tetrachloride may be reacted with vinyl chloride in the presence of an iron-containing compound and tributylphosphate to produce a product stream. Then, in separation scheme (A), the reactor product stream may be distilled into a top stream comprising volatile reactants that are recycled, and a bottom stream that contains the HCC240f product and the catalyst complex. This bottom stream may be further distilled into a second top stream comprising the desired product, and a second bottom stream containing the catalyst complex, which is recycled. Alternatively, in separation scheme (B), the reactor product stream may be distilled into a top stream that contains the desired product and a bottom stream that contains the catalyst components. This bottom stream may be recycled, while the top stream may be distilled into a second top stream containing volatile reactants, which are recycled, and a second bottom stream, which contains the desired halocarbon product.

But separation scheme (A) would subject the catalyst components to two distillation steps before they are recycled into the reactor. Each distillation step stresses the catalyst components, causing degradation. In a process based on the reaction of carbon tetrachloride with vinyl chloride in the presence of iron chlorides and tributylphosphate, such as that described herein, the catalyst degrades by a process of chemical reactions that increase in extent with temperature, time, and catalyst concentration. The bottoms stream from the first distillation of scheme (A) is large, since it contains the desired product of the reaction. This means that the equipment used for both distillation steps of scheme (A) must be large, and the residence times in both stills must be relatively long. The catalyst components are recovered as the bottoms from the second still, where the temperature is high, the catalyst concentration is high, and the liquid residence time is long.

Separation scheme (B) is better, since the catalyst is recovered and recycled as the bottoms from the first tower. Even so, this first tower is necessarily large, since it handles the whole product load, going overhead, and so the liquid residence time is long. If one wishes to recover most of the product, then the concentration of catalyst components in the bottoms of the first tower is high, and the temperature is high. These conditions again promote rapid degradation of the catalyst. Furthermore, the reaction of the invention results in the production of two main undesired byproducts—1,1,1,3,5,5-hexachloropentane (HCC470jfdf) and 1,1,3,3,5,5-hexachloropentane (HCC470nfaf). These components, being less volatile than the desired HCC240f (b.p. 179 C), tend to stay with the catalyst components, which are either non-volatile, or have very high boiling points (tributylphosphate boils at 289 C.). Therefore, if the bottoms of the first tower are recycled, this stream carries with it a considerable amount of the hexachloropentane byproducts. These components, in the recycle stream, are harmful to the desired reaction in two ways: first, they dilute the reactants, thereby reducing the reaction rate. Second, they can react with vinyl chloride, thus consuming valuable feedstock, and produce further undesired by-products.

What is needed is a method of recovering the HCC240f, free of the hexachloropentane byproducts, which minimizes the stress placed on the catalyst components, and which separates, as much as possible, the catalyst components from the hexachloropentanes.

Wilson et al (U.S. Pat. No. 6,313,360) is directed to a process for the production of 1,1,1,3,3-pentachloropropane by reacting carbon tetrachloride (CCl$_4$) and vinyl chloride in the presence of a catalyst mixture (organophosphate solvent, iron metal and ferric chloride). The process of the herein disclosed invention in superior to that of the Wilson et al in that the conditions employed are more economic and the activity of the catalyst is maintained to a far greater degree.

The prior art (Wilson et al) describes a single-stage catalyst recovery system. In prior art processes high temperature and long residence time tend to cause degradation of the catalyst. The inventors have found that by adding a second distillation step and modifying the conditions of the first distillation step a surprisingly high percentage of the desired product (1,1,1,3,3-pentachloropropane) can be recovered in pure form and the catalyst is maintained in exceptionally useful form.

The inventors have succeeded in producing a much more highly concentrated catalyst recycle stream than that embodied in U.S. Pat. No. 6,313,360. They have also succeeded in recovering a significantly higher percentage of the 1,1,1,3,3-pentachloropropane produced. Based on the prior-art work, in lab and pilot plant, the inventors have unexpectedly retained significant amounts of active catalyst in their recycle process.

OBJECTS OF THE INVENTION

A main object of the invention is to produce a process that will maximize the recovery of the catalyst.

A further object of the invention is to perform the process under relatively mild conditions.

A significant object of this invention is to provide a process for producing halohydrocarbons under economic conditions.

Another object of this invention is to produce a haloalkane production process that preserves the catalyst.

These and other objects of the present invention will become apparent from a reading of the following specification taken in conjunction with the enclosed drawings.

SUMMARY

The herein disclosed invention provides an improved method for catalyst recovery and recycle and for product recovery in a high capacity continuous process for the manufacture of a desired haloalkane product by the addition reaction of a haloalkane with a haloalkene, in the presence of a catalyst system comprised of ferrous chloride, ferric chloride, and a trialkylphosphate. The catalyst components tend to degrade when stressed by high temperature, long residence times, and high concentrations. The instant invention mitigates this problem. The catalyst components are recovered in a two-stage distillation system, in which the first stage performs a rough cut separation between the catalyst components and the desired product, under relatively mild conditions that do not stress the catalyst components unduly, and the second stage performs a more nearly complete separation between the catalyst components and the desired product, using relatively small equipment and short residence time, to stress the catalyst components as little as possible, given the relatively higher temperature and concentration of the catalyst components in this unit.

The starting materials for carrying out the process of the instant invention are carbon tetrachloride ($CCl_4$), and vinyl chloride in the presence of a catalyst system comprised of ferric chloride, ferrous chloride, and metallic iron in a trialkylphosphate solvent, tributylphosphate being the preferred trialkylphosphate solvent. While 1,1,1,3,3-pentachloropropane is the principle and desired product produced, other byproducts such as 1,1,1,3,5,5 hexachloropentane, 1,1,3,3,5,5 hexachloropentane and hexachloroethane are also produced.

A preferred method for preparing 1,1,1,3,3-pentachloropropane is described. Vinyl chloride and carbon tetrachloride are reacted in the presence of tributylphosphate and iron metal in the reactor and a reactor effluent containing halohydrocarbons and catalyst components are sent to the first refluxed evaporator. In the first refluxed evaporator, the reactor effluent is split into distillate and bottom fractions. The distillate contains mainly 1,1,1,3,3-pentachloropropane produced and lower boiling compounds from a heavy bottom fraction. The bottom fraction contains a small fraction of the 1.1.1.3.3-pentachloropropane produced, and higher boiling materials, including catalyst components. Serious degradation of catalyst components is avoided by operating the evaporator under partial vacuum at a relatively low bottom boiling temperature and at a fairly short liquid residence time. The second refluxed evaporator removes most of the remaining 1,1,1,3,3-pentachloropropane from the bottom liquid from the first evaporator, producing a new bottom fraction containing the catalyst components in a form highly suitable for recycle to the reactor. Serious degradation of the catalyst in this tower is avoided by operating at low temperature, and at even lower liquid residence time than in the first tower.

In its broadest aspect, the herein disclosed invention involves a process for preparing a desired haloalkane, as for example, 1,1,1,3-tetrachloropropane, 1,1,1,3,3,3-hexachloropropane or 1,1,1,3-tetrachlorobutane by contacting a haloalkene or alkene, such as, vinylchloride, ethylene, propylene, butylene or 1,1-dichloroethylene with a haloalkane such as carbon tetrachloride, chloroform or 1,1,1-trichlorethane in the presence of effective amounts of catalyst components, ferrous chloride, ferric chloride, and a trialkylphosphate compound, under conditions effective to promote an addition reaction and to form a product stream containing said haloalkane product, higher boiling haloalkane byproducts, unreacted feedstocks, and catalyst components, and separating the desired haloalkane product from the high-boiling undesired haloalkane byproducts and the catalyst components using a two-stage catalyst recovery unit (CRU), wherein, the bottom fraction from the first stage flows into the second stage, and the overhead fractions from the two stages are combined for further purification steps, and the first stage of the CRU recovers, in the distillate, between 50 and 90% of the desired haloalkane product contained in the reactor effluent, leaving more than 98% of the high-boiling undesired haloalkane byproducts in the bottom fraction, and the second stage of the CRU recovers, in the distillate, more than 70% of the remaining desired haloalkane product, leaving more than 98% of the high-boiling undesired haloalkane byproducts in the bottom fraction, together with the catalyst components, and recycling most of the bottom fraction from the second stage of the CRU to the reactor, and purging a small fraction of it from the system to control byproduct concentrations in the reactor and to avoid excessive catalyst degradation. In the process the first stage of the CRU roughly distills the desired haloakane product and lower boiling components from the undesired high boiling haloalkane byproducts, higher boiling components, and catalyst components, producing a bottom fraction containing between 35 and 75 percent of the desired haloalkane product and wherein the second stage further separates the bottoms stream from the first stage into an overhead stream containing the desired haloalkane product and less than 2 wt. percent of the undesired high-boiling haloalkane byproducts, and produces a bottoms catalyst fraction suitable for recycle to the reactor, which contains less than 25 wt. percent of the desired haloalkane product. The first stage of the CRU can be operated at 10 to 50 Torr bottom pressure, and at 160–240 degrees F. bottom temperature, and the liquid residence time, defined as the ratio of the volume of liquid contained in the bottom of the tower to the volumetric liquid flow rate from the bottom of the tower, is less than five days, and the second stage of the CRU is operated at 3 to 15 Torr bottom pressure, and at 180–260 degrees F bottom temperature, and the liquid residence time is less than 12 hours. More specifically, the first stage of the CRU can be operated at less than 215 F. bottom temperature, and at less than five days liquid residence time, and the second stage of the CRU is operated at less than 240 F. bottom temperature, and at less than 12 hours liquid residence time. Note, also, that under specific conditions, the first stage of the CRU can be operated at 10 to 50 Torr bottom pressure, and at 160–240 F. bottom temperature; the second stage of the CRU can be operated at 3 to 15 Torr bottom pressure and at 180–260 F. bottom temperature; the first stage of the CRU can be operated at less than 215 F. bottom temperature, and the second stage of the CRU can be operated at less than 240 F. bottom temperature; the liquid residence time in the first stage is less than five days and the liquid residence time in the second stage is less than 12 hours; the liquid residence time in the first stage is less than 24 hours and the liquid residence time in the second stage is less than six hours; the liquid residence time in the second stage is no more than 20% of the liquid residence time of the first stage, and the temperature of the second stage bottom liquid is no more than 25 degrees F. hotter than the temperature of the first stage bottom liquid. In a specific embodiment of this invention, the desired haloalkane product is 1,1,1,3,3-pentachloropropane, the haloalkene feedstock is vinyl chloride, the haloalkane feedstock is tetrachloromethane, the main undesired high-boiling haloalkane byproducts are 1,1,1,3,5,5-hexachloropentane and 1,1,3,3,5,5-hexachloropentane, and the trialkylphasphate compound is tributylphosphate. In a special aspect of the invention, there is carried out a process for preparing 1,1,1,3,3-pentachloropropane comprising, (a) reacting carbon tetrachloride and vinyl chloride in the presence of a catalyst, and then (b) distilling the reaction products of step (a) using temperature and pressure conditions that do not materially destroy the catalyst and also produce a significant amount of 1,1,1,3,3-pentachloropropane. More specifically the invention encompasses a method for generating 1,1,1,3,3-pentachloropropane comprising, (a) reacting carbon tetrachloride with vinyl chloride in the presence of a catalyst comprising elemental iron, ferric chloride, and tributylphosphate, producing a reactor effluent, and (b) distilling the reactor effluent, separating 1,1,1,3,3-pentachloropropane and lower boiling components from high boiling components at a temperature and pressure which do not substantially inactivate the catalyst, and producing a bottom fraction containing the catalyst components and less than 50% of the 1,1,1,3,3-pentachloropropane contained in the reactor affluent from step (a), and (c) distilling the bottom fraction from step (b) to recover overhead at least 70% of the 1,1,1,3,3-pentachloropropane remaining in the bottom fraction from step (b), and producing a new bottom fraction suitable for recycle to the reactor, and (d) combining the distillate fractions of steps (b) and (c) for further purification of the 1,1,1,3,3-pentachloropropane product. Also, envisioned by this invention is a method for producing a purified halohydrocarbon and a catalyst recycle stream comprising (a) reacting carbon tetrachloride and an olefin in the presence of a catalyst to prepare a mixture of a desired halohydrocarbon and catalyst, (b) processing the desired halohydrocarbon and catalyst in a first refluxed evaporator employing a partial vacuum and moderate temperature effective to prevent excessive catalyst degradation, recovering a substantial fraction of the desired halohydrocarbon overhead, and producing a bottom fraction containing the catalyst components, (c) processing the bottom fraction from step (b) in a second refluxed evaporator employing a partial vacuum, moderate temperature, and shortened liquid residence time effective to prevent excessive catalyst degradation, recovering a substantial fraction of the remaining desired halohydrocarbon overhead, and producing a bottom fraction containing the catalyst components in a state suitable for substantial recycle to the reactor, and (d) further processing the combined overhead fractions from the first and second refluxed evaporators of steps (b) and (c) to produce a purified halohydrocarbon stream. The purified halohydrocarbon recovered is 1,1,1,3,3-pentachloropropane, and the olefin fed is vinyl chloride. The first refluxed evaporator is operated at about 10 to 50 Torr, with a bottom temperature of about 160 to 240 F., and the second refluxed evaporator is operated at about 3~15 Torr, with a bottom temperature of about 180–260 F. The liquid residence time in the first refluxed evaporator is less than 24 hours and the liquid residence time in the second refluxed evaporator is less than about six hours. The first refluxed evaporator has a pressure of about 20 Torr and a temperature of about 187 F., and the second refluxed evaporator has a pressure of about 5 Torr, and a temperature of about 207 F. An elegant embodiment of the invention involves a process for preparing a desired haloalkane produce comprising: (a) contacting a haloalkene and a haloalkane feedstock in the presence of effective amounts of catalyst components ferrous chloride, ferric chloride, and a trialkylphosphate compound, under conditions effective to promote an addition reaction and to form a reactor effluent containing said haloalkane product, higher boiling haloalkane byproducts, unreacted feedstocks, and catalyst components, and (b) separating the desired haloalkane product from the high-boiling undesired haloalkane byproducts and the catalyst components using a two-stage catalyst recovery unit, wherein, (i) the bottom fraction from the first stage flows into the second stage, and (ii) the first stage of the CRU recovers, in the distillate, between 50 and 90% of the desired haloalkane product contained in the reactor effluent, leaving more than 98% of the high-boiling undesired haloalkane byproducts in the bottom fraction, and (iii) the second stage of the CRU recovers, in the distillate, more than 70% of the remaining desired haloalkane product, leaving more than 33% of the high-boiling undesired haloalkane byproducts in the bottom fraction, together with the catalyst components, and (iv) further distilling the overhead fraction from step iii. to produce a new overhead fraction containing the desired haloalkane product and less than 1 wt. % of the high-boiling undesired haloalkane products and a new bottom fraction containing the undesired haloalkane produce, and (v) disposing or otherwise using the bottom fraction of step iv., and (c) combining the overhead fraction of step iv. with the overhead fraction of step ii. for further purification, and (d) recycling most of the bottom fraction from step iii. to the reactor, and purging a small fraction of it from the system to control byproduct concentrations in the reactor and to avoid excessive catalyst degradation.

Abbreviations and Terms

| | |
|---|---|
| HCC240f = | 1,1,1,3,3-pentachloropropane |
| HCC470jfdf = | 1,1,1,3,5,5-hexachloropentane |
| HCC470nfaf = | 1,1,3,3,5,5-hexachlosopentane |
| HCE = | hexacloroethane |
| HCC470s = | hexachoropentanes |
| TBP = | tributyl phosphate |
| VnCl = | vinyl chloride |
| $CCl_4$ = | carbon tetrachloride |

The terms, "distillation tower", "refluxed evaporator", and "catalyst recovery unit are used interchangeably throughout the remaining text. These terms mean the same thing when the context is catalyst recovery.

Figure 2:
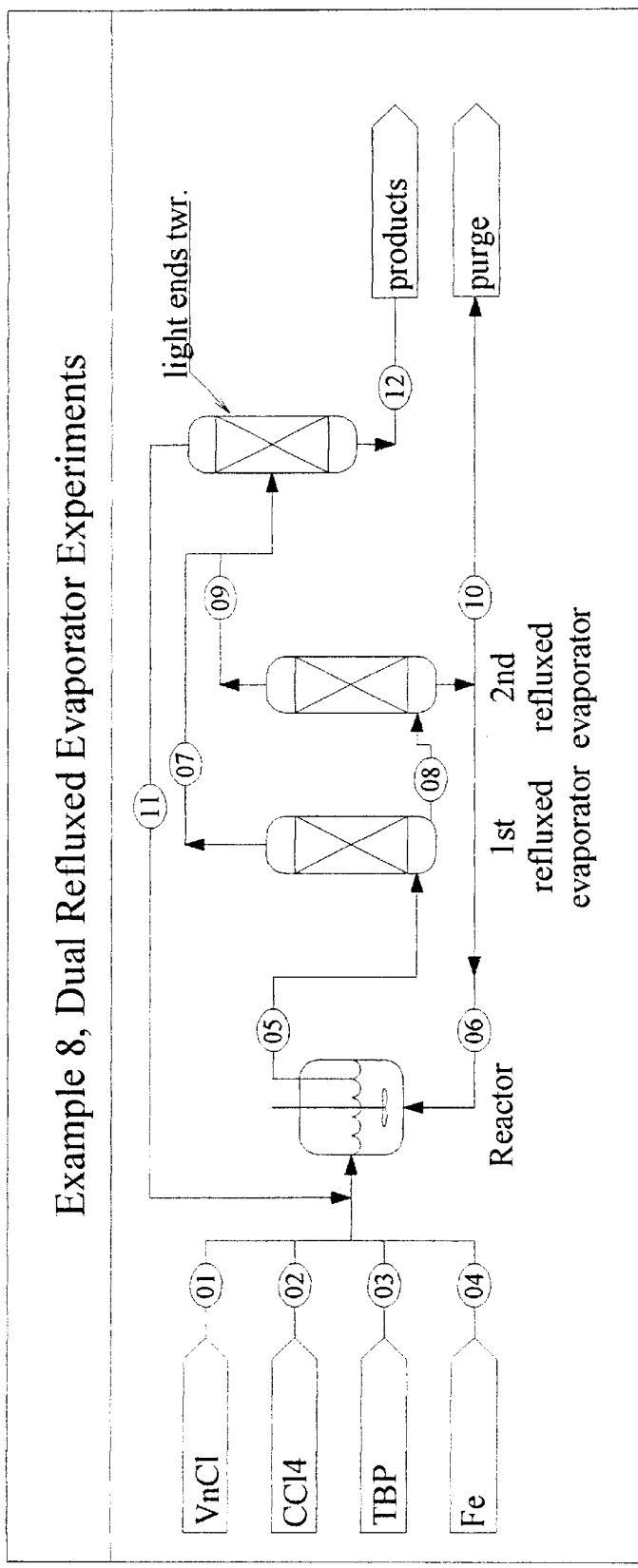
FIG. 2 is a schematic representation of the process of this invention. Example 8 below.

With reference to FIG. 2 there is shown a schematic representation of the process of this invention. Vinyl chloride, carbon tetrachloride, tributylphosphate and iron represented as (01–04) are reacted in the reactor and sent (05) to the first refluxed evaporator and treated under temperature and vacuum conditions to produce a distillate (07) and a bottoms fraction (08). The bottoms fraction (08) is sent to a second refluxed evaporator and treated under different temperature, vacuum, or liquid residence time conditions, to produce a distillate (09) and a bottoms fraction which is purged (10) or returned to the reactor (06) for reuse. The distillate (07) can be further distilled in a light ends tower to produce light ends (11), a portion of which is returned to the reactor and a stream containing most of the desired product (12), which may be subjected to further purification steps.

The components of the various process streams is as follows: Referring to the process stream numbers shown in FIG. 2, streams 01, 02, 03, and 04 are the pure feedstocks. Stream 05, reactor effluent, contains all of the components found elsewhere in the process. Stream 07 contains most of the HCC240f produced in the reactor, and most of those components of the reactor effluent that boil at temperatures lower than that of HCC240f. Stream 08 contains a small fraction of the HCC240f produced, together with the components of the reactor effluent that boil higher that HCC240f, including all of the catalyst components. Catalyst components include metallic iron, ferric chloride, ferrous chloride, tributylphosphate, and phosphorus-containing organic compounds. The latter are produced by degradation of the tributylphosphate. Ferric chloride and ferrous chloride are produced in the reactor, from the metallic iron.

Stream 09 contains mostly HCC240f, with traces of hexachloropentanes. Streams 06 and 10 contain hexachloropentane byproducts, tributylphosphate, tributylphosphate degradation products, ferric chloride, and a few weight percent of HCC240f. Stream 11 contains mostly carbon tetrachloride, with traces of vinyl chloride and other light ends, such as chloroform, 1-chlorobutane, 1,1,2-trichloroethane, and tetrachloropropene. Stream 12 contains mainly HCC240f and an undesired byproduct of the reaction, HCC-240db. There may also be trace amounts of hexachloroethane, hexachlorobutadiene and hexachloropentanes in this stream. The exact composition of these streams varies, depending on feed ratios, conversion, distillation conditions, etc.

The light ends tower is used to separate lighter components from HCC240f product. The distillate fraction of the light ends tower contains unconverted vinyl chloride, unconverted carbon tetrachloride, and other light byproducts. A portion of the light distillate may be recycled to the reaction step, improving feedstock conversion for the overall process. Examples of light byproducts include chloroform, 1-chlorobutane, 1,1,2-trichloroethane, and tetrachloropropene.

A representative list of significant reactor effluent components, grouped as to boiling point range, is shown below.

| | |
|---|---|
| B.P. lower than HCC240f | chloroform, 1-chlorobutane, 1,1,2-trichloroethane, 1,1,3,3-tetrachloropropene, carbon tetrachloride, vinyl chloride |
| B.P. roughly the same as HCC240f | hexachloroethane |
| B.P. higher than HCC240f or non-boiling | 1,1,1,3,3,5,5-heptachloropentane, 1,1,3,3,5,5-hexachloropentane, tributylphosphate, tributylphosphate degradation products that contain phosphorus, ferric chloride, metallic iron, hexachlorobutadiene, 1,1,1,2,3-pentachloropropane. |

DESCRIPTION OF THE INVENTION

The herein disclosed invention provides a high capacity, continuous process for the production of 1,1,1,3,3-pentachloropropane (HCC240f) by the reaction of carbon tetrachloride with vinyl chloride (VnCl) in the presence of a catalyst system comprised of ferric chloride, ferrous chloride, metallic iron, and trialkylphosphate. The most favored trialkylphosphate is tributylphosphate. In a continuous reactor of the invention, the reactor effluent contains the desired product, HCC240f, unreacted feeds $CCl_4$ and VnCl, undesired byproducts of the reaction 1,1,1,3,5,5-hexachloropentane, 1,1,3,3,5,5-hexachloropentane, and hexachloroethane (HCE), dissolved iron compounds and phosphorus compounds, including trialkylphosphate. The catalyst system is essentially non-volatile, compared with other components of the reactor effluent. Most of the metallic iron is retained, or consumed, in the reactor.

In a favored prior-art process, the reactor effluent is distilled in a single-stage catalyst recovery unit, which separates the HCC240f and lower-boiling components overhead from the hexachloropentanes (also called HCC470s) and less volatile materials, below. This distillation is done at low pressure, to avoid decomposition of various components of the reaction mixture. The overhead stream is then separated by further distillation stages into feed materials, for recycle, and product, for sale. The bottom stream from the catalyst recovery unit contains all of the catalyst components, except metallic iron, and is mostly recycled into the reactor. However, a small portion is purged to prevent the accumulation of too much hexachloropentane and degraded catalyst components. The trialkylphosphate degrades more at higher temperature, at higher concentrations of the catalyst components, and with greater residence time. The catalyst recovery unit of this prior-art process performs a double duty, then. It separates the desired product from higher boiling materials, especially the hexachloropentanes. And it recovers catalyst components in a form that is suitable for recycle.

Both of these functions can indeed successfully be performed with a single distillation tower. However, it has been found in practice that there are disadvantages of this procedure. The most important goal for the tower is to recover as much as possible of the desired product, HCC240f, from the unit. This means that the tower must operate at a temperature higher than the boiling temperature of pure HCC240f and close to the boiling temperature of a mixture of hexachloropentanes at the chosen distillation pressure. The distillation pressure is largely fixed by the capital cost, since the size of the tower increases rapidly with decreasing pressure. Several design constraints fix the minimum practical size of the tower. In order for the process to be stable the tower must contain sufficient in-process material to absorb flow surges. The tower must also distill compounds with a very broad boiling point range. Further, since most of the tower feed is recovered as distillate at low pressure, it must be large. This means that the liquid residence time is long. The high temperature and long residence time tend to aggravate the degradation of the catalyst. In practice, in order to limit such degradation to acceptable levels, the tower must be operated at a low temperature, so that considerable HCC240f remains in the bottoms liquid, where it will either be recycled back into the reactor or, eventually, be purged from the system.

A second important goal for the tower is to produce a stream of liquid that contains the catalyst components in a form suitable for recycle. However, this goal is not easily satisfied by using such simple equipment. As mentioned above, the bottom material necessarily contains a considerable amount of HCC240f. But the recycle of HCC240f into the reactor is not desired, since there it reacts with costly VnCl to produce HCC470nfaf. It also dilutes feed stocks and catalyst components, reducing the space-time yield of the reactor. Further, the presence of large amounts of hexachloropentanes in the recycle stream is also undesired, because they, too, react with VnCl and reduce the space-time yield through dilution. What is wanted for recycle is a liquid stream containing the catalyst components in high concentration. Finally, for the reasons discussed above, the catalyst has degraded in this unit, due to the harsh conditions prevailing there.

We have now found that by adding just one more relatively small distillation step, and by modifying the duties of the first step, a surprisingly high percentage of the desired product can be recovered pure, while producing a stream that contains the catalyst components in an exceptionally useful form. This two-stage catalyst recovery system also greatly reduces the amount of material that is purged. In one form of the invention, the reactor effluent is distilled in a first stage distillation column which separates HCC240f and lower-boiling components from the hexachloropentanes and higher-boiling components. The mission of this column is modified from the prior art design, however, in that the major goal for this unit is not to recover nearly all of the HCC240f, but merely to recover a substantial fraction of it. Further, there is no attempt to produce an ideal catalyst recycle stream in this unit. Therefore, the equipment can be operated at a relatively lower temperature than the single unit of the prior-art catalyst recovery unit, and sized smaller, to minimize catalyst degradation.

Then the bottom stream from this first stage passes into a second distillation stage, whose two-fold mission is to recover the rest of the HCC240f contained in the stream, overhead, while producing an improved catalyst recycle stream. Since this unit handles only a small fraction of the HCC240f produced, and none of the unconverted feed stocks, it can be sized relatively very small indeed, so that liquid residence time can be very short. This surprisingly makes it possible to economically recover virtually all of the HCC240f contained therein, in a form that contains only insignificant amounts of hexachloropentanes, while producing a stream that contains the catalyst components in a highly concentrated and more useful form. This improved catalyst recycle stream contains almost no HCC240f and reduced amounts of the hexachloropentanes, compared to the prior art.

General Description

Two refluxed evaporators are arranged in series with the second being fed the bottom fraction from the first. The first refluxed evaporator is fed the product stream(s) from 1,1,1,3,3-pentachloropropane reactor(s). The reactor product stream(s) contain light components, 1,1,1,3,3-pentachloropropane, catalyst components, and heavy components. Light components have greater vapor pressure than 1,1,1,3,3-pentachloropropane. Heavy components have lower vapor pressure than 1,1,1,3,3-pentachloropropane. The first flash tower separates the reactor product into distillate and bottom fractions. Light components and most of the 1,1,1,3,3-pentachloropropane are recovered in the distillate fraction. Catalyst components, heavy components, and some 1,1,1,3,3-pentachloropropane are recovered in the bottom fraction.

The second refluxed evaporator separates the bottom fraction of the first refluxed evaporator into distillate and bottom fractions. Most of the 1,1,1,3,3-pentachloropropane remaining in first refluxed evaporator's bottoms is recovered in the distillate fraction. The catalyst components and substantially all of the heavy components are recovered and concentrated in the bottom fraction. A fraction, between 5 and 15 percent, of the second refluxed evaporator's bottoms are purged to control degraded catalyst and heavy component accumulation. The rest of second refluxed evaporator's bottoms are recycled to the 1,1,1,3,3-pentachloropropane reactor(s).

Catalyst recycling benefits the overall process by decreasing the purge stream and decreasing fresh catalyst component feed consumption. The recycled material contains ferric chloride and TBP. Except for a start-up charge, fresh ferric chloride feed may be eliminated entirely. Fresh TBP feed is decreased greatly and elemental iron feed is also decreased. Catalyst recycling is limited by TBP degradation.

While not wishing to be bound by theory, the degradation process begins with TBP molecules losing one butyl group each. Thus, TBP is converted to dibutylphosphate (DBP). DBP combines with iron chlorides to form phospho-organic iron salts. Catalyst components are eventually converted to inert matter, theoretically starting with this process. The extent of catalyst degradation is a complex function of temperature, catalyst concentration, and residence time. Catalyst components are concentrated in the bottom fraction of each refluxed evaporator, tending to increase catalyst degradation.

Operating the refluxed evaporators under partial vacuum decreases bottom temperature and decreases catalyst degradation. Designing refluxed evaporators to operate with minimal bottom liquid volume will decrease residence time and decrease catalyst degradation. However, there are practical limitations to how small the liquid volume can be. Enough liquid must be present in each refluxed evaporator to absorb and dampen the effects of feed surges. The evaporator sections must be designed with sufficient cross-sectional area to allow vapor-liquid separation. The refluxed sections must be designed for minimal pressure drop to allow the evaporation section to operate at low pressure.

The distillate fraction of both refluxed evaporators is combined and fed to a two-step distillation process train. The first distillation step separates light components from 1,1,1,3,3-pentachloropropane. Light components are recovered in the distillate fraction of the first distillation step. This fraction contains unconverted carbon tetrachloride, unconverted vinyl chloride, and other light components. Most of this material is recycled to the reactor(s). The remainder is purged to control the accumulation of light byproducts. The bottom fraction of the first distillation contains 1,1,1,3,3-pentachloropropane and heavy components. This stream is fed to the second distillation step. The second distillation step separates purified 1,1,1,3,3-pentachloropropane from the heavy components.

The reactor(s) are fed vinyl chloride, carbon tetrachloride, iron, TBP, recycled distillate from the first distillation step, and recycled bottoms from the second refluxed evaporator. In the reactor, ferric chloride from the bottom recycle stream reacts with iron to form ferrous chloride. Ferrous chloride is part of a catalytic complex, also made up of ferric chloride, TBP, and possibly other phospho-organic iron salts. The complex is a Kharasch catalyst and facilitates the combination reaction of carbon tetrachloride with vinyl chloride to make 1,1,1,3,3-pentachloropropane.

EXAMPLES

Example 1

This test demonstrates the stress upon the catalyst system when subjected to high temperature for extended periods of time. A sample of ordinary prior-art catalyst recycle material was obtained from the pilot plant HCC240f reactor and distillation system, which employed prior-art single-stage catalyst recovery. This recycle material contained about 54 wt % HCC240fa, 16 wt % HCC470jfdf, 22 wt % HCC470nfaf, 2 wt % TBP, and 1% FeCl3. The balance from 100%, about 5 wt %, was primarily unanalyzed material, presumed to be phosphorus-containing compounds from the degradation of TBP. Approximately 5000 grams of this prior-art catalyst recycle material was flash distilled in the lab in a single-stage glass distillation apparatus at approximately 10 Torr pressure. The boiling bottoms material was below 98 degrees C. for 1.5 hours (fraction A), 98–109 degrees C. for 4 hours (fraction B), 110–125 degrees for 0.7 hours (fraction C), and 125–144 degrees C. for 1 hour (fraction D). Total heating time was approximately 7.3 hours. The composite overhead sample collected during fraction D contained 10.7 wt % HCC240f, 35.5 wt % HCC470jfdf, and 49.0 wt % HCC470nfaf. The mobile black liquid remaining in the distillation pot represented the concentrated catalyst recycle material. Shortly after completion of fraction D, the bottoms material underwent catastrophic decomposition, forming a solid, black mass, accompanied by the rapid release of large quantities of non-condensable gas. This illustrates the most extreme stressing of the recycle catalyst resulting from high temperature exposure for long periods of time.

Example 2

This test demonstrates the reduced stress upon the catalyst system that results from decreasing the maximum temperature. Approximately 5000 grams of ordinary prior-art catalyst recycle material from the pilot plant HCC240f reactor and distillation system was flash distilled in the lab as before at approximately 10 torr pressure. The boiling bottoms material was below 87 degrees C. for 1.8 hours (fraction A), 87–115 degrees for 2.3 hours (fraction B), 115–123 degrees C. for 0.9 hours (fraction C), and 123–125 degrees for about 1.5 hours (fraction D). Total heating time was approximately 6.5 hours. The composite overhead sample collected during fraction D contained 1.3 wt % HCC240f, 38.9 wt % HCC470jfdf, and 56.0 wt % HCC470nfaf. The mobile black liquid remaining in the distillation pot represented the concentrated catalyst recycle material. No catastrophic decomposition of the bottoms material occurred in this experiment. This illustrates that lower temperatures prevent catastrophic decomposition of the bottoms.

Example 3

This test demonstrates the reduced stress upon the catalyst system that results from decreasing the residence time. Approximately 1200 grams of ordinary prior-art catalyst recycle material from the pilot plant HCC240f reactor and distillation system was flash distilled in the lab as before at approximately 15 Torr pressure. The boiling bottoms material was below 84 degrees C. for 0.4 hours, 84–120 degrees for 0.4 hours, and 120–145 degrees for 0.6 hours. Total heating time was approximately 1.4 hours. The composite overhead sample collected during the entire process contained approximately 50 wt % HCC240f, 15 wt % HCC470jfdf, and 30 wt % HCC470nfaf. The mobile black liquid remaining in the distillation pot represented the concentrated catalyst recycle material. No catastrophic decomposition of the bottoms material occurred in this experiment. This illustrated that shorter residence times prevent catastrophic decomposition of the bottoms at 145 degrees C.

Example 4

This test demonstrates the stress upon the catalyst system when subjected to high temperature for even short periods of time. Approximately 1000 grams of ordinary prior-art catalyst recycle material from the pilot plant HCC240f reactor and distillation system was flash distilled in the lab as before at approximately 15 Torr pressure. The boiling bottom material was below 94 degrees C. for 0.5 hours, and 94–155 degrees for 0.8 hours. Total heating time was approximately 1.3 hours. The bottom material underwent catastrophic decomposition at the end of the flash distillation, forming a solid, black mass, accompanied by the rapid release of large quantities of non-condensable gas. This illustrates that extreme stressing of the recycle catalyst results from high temperature exposure for even short periods of time.

Example 5

This test demonstrates the surprising catalytic effectiveness of extraordinarily concentrated distillation bottoms material, such as that which would be obtained from the second distillation tower of a two-stage catalyst recovery system which is the subject of this invention. A sample of ordinary prior-art catalyst recycle material was obtained from our pilot plant HCC240f reactor and distillation system, which employs a prior-art single-stage catalyst recovery system. More precisely, the reactor effluent enters a distillation tower, where most of the HCC240f and lower-boiling materials go overhead and hexachloropentanes and higher boiling materials go out the bottom. This prior-art catalyst recycle material was then further distilled in the lab, at about 13 Torr or lower pressure, and at about 147 C or lower bottoms temperature. The still residue from this distillation was a mobile black liquid, which contained 0.05% HCC240f, 10 wt % HCC470jfdf, 40 wt % HCC470nfaf, 15 wt % TBP, and 13 wt % FeCl$_3$. The balance from 100%, about 22 wt %, was unanalyzed material, presumed to be phosphorus-containing compounds that result from the degradation of TBP.

An aliquot of this extraordinarily concentrated material, 4.6 g, was combined with 0.17 g fresh TBP, 57.83 g CCl$_4$, 0.235 g granular iron metal, and 15.1 g VnCl in a Hastalloy C 100 ml autoclave reactor. The resulting FeCl$_3$/VnCl feedratio was 0.015 mole/mole. The mixture was vigorously stirred at 110 C for 1.22 hours. At the end of this time, the pressure had fallen to 27 psig, indicating completion of the reaction. The reactor was cooled.

A sample of the reactor contents was then analyzed by gas chromatography, and a mass balance was calculated. The VnCl conversion was 93.8%, and the space-time yield of HCC240f was 5.6 lb hr$^{-1}$ gallon$^{-1}$, where the volume refers to the volume of liquid contained in the reactor. The selectivities were calculated as the net moles of byproduct produced, per mole of HCC240f produced, expressed as a percentage. The measured selectivities were 5.7%, 1.1%, and 0.011%, respectively, for HCC470jfdf, HCC470nfaf, and HCE.

Example 6

This is a comparison test using the bottoms from a prior art single-stage catalyst recovery system as the recycle catalyst feedstock for a HCC240f reactor. A sample of first distillation tower bottoms was obtained from our pilot plant reactor and distillation system. This material contained 42 wt % HCC240f, 14 wt % HCC470jfdf, 31 wt % HCC470nfaf, 3.3 wt % TBP, and 2.8 wt % FeCl$_3$. A mixture of 21.5 g. of this recycle catalyst material with 0.17 g fresh TBP, 57.56 g CCl$_4$, 0.240 g granular iron metal, and 15.4 g VnCl was placed into the 100 ml autoclave. The resulting FeCl$_3$/VnCl feedratio was then 0.015 mole/mole. The mixture was stirred at 110 C for 2.0 hours. At the end of this time, the pressure had fallen to 24 psig, indicating completion of the reaction. The reactor was cooled and sampled.

Analysis of the reactor contents indicated that the VnCl conversion was 95.5%, the space-time yield of HCC240f was 3.0 lb hr$^{-1}$ gallon$^{-1}$, and the selectivities to HCC470jfdf, HCC470nfaf, and HCE were 6.8%, 2.2%, and 0.009%, respectively. Hence, the selectivities for unwanted byproducts HCC470jfdf and HCC470nfaf were worse than observed in Example using the extraordinarily concentrated recycle catalyst feedstock, and the space-time yield of HCC240f was lower, too.

Example 7

This is a comparison test without recycle catalyst, which illustrates some of the ill effects of not recycling FeCl$_3$. A mixture of 0.35 g fresh TBP, 58.97 g CCl$_4$, 0.241 g granular iron metal, and 15.9 g VnCl was placed into the 100 ml autoclave. The resulting (total TBP)/VnCl feed ratio was then 0.0052 mole/mole. This mixture was stirred at 110 C for 2.77 hours. At the end of this time, the pressure had fallen to 27 psig, indicating completion of the reaction. The reactor was cooled and sampled.

Analysis of the reactor contents indicated that the VnCl conversion was 99.6%, the space-time yield of HCC240f was 1.1 lb hr$^{-1}$ gallon$^{-1}$, and the selectivities to HCC470jfdf, HCC470nfaf, and HCE were 35%, 1.1%, and 0.870%, respectively. Thus, by comparison with Example, the space-time yield without recycle catalyst was greatly suppressed, and the selectivity to undesired HCC470jfdf was greatly increased.

Example 8

Figure 1:
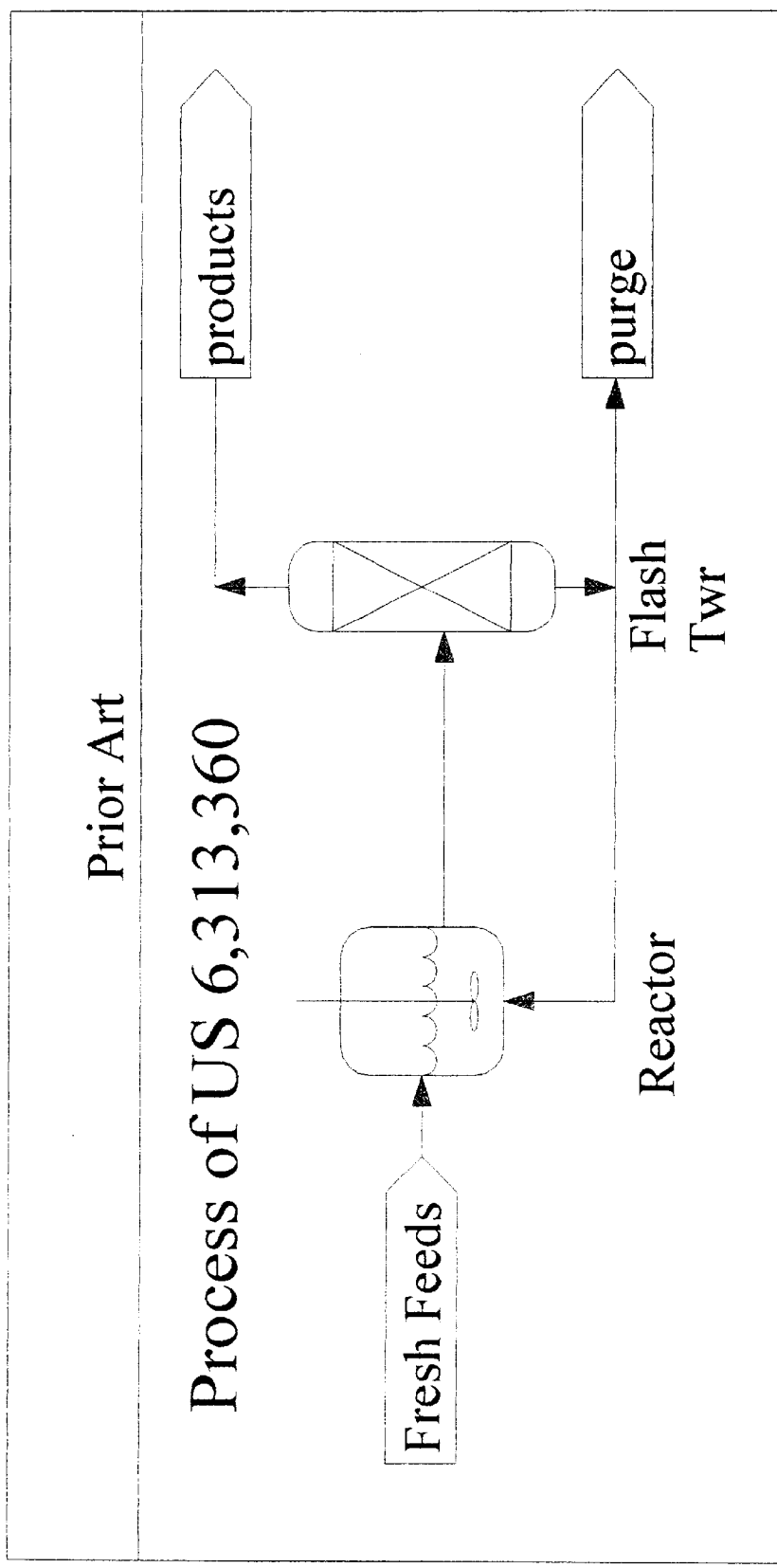
FIG. 1 is a schematic representation of prior art patent U.S. Pat. No. 6,313,360.

In the prior art (Wilson et al, FIG. 1) a 1,1,1,3,3-pentachloropropane pilot plant was operated using a single refluxed evaporator. The single refluxed evaporator split the reactor product stream into distillate and bottom fractions. Most of the bottom stream was recycled to the reactor while a portion was purged to control heavy byproduct and degraded catalyst accumulation. Using a single refluxed evaporator, the best sustainable operating conditions had a purge to product ratio of 0.07 pounds bottoms purge per pound of 1,1,1,3,3-pentachloropropane recovered in the distillate fraction. Under these conditions, approximately half of the purge's composition was 1,1,1,3,3-pentachloropropane.

A second refluxed evaporator was installed in a similar pilot plant, resulting in a pilot plant implementation of the process of this invention (in this regard see FIG. 2). The equipment was arranged to feed the bottoms from the first refluxed evaporator to the second. The purge and recycle streams were taken from the second refluxed evaporator bottoms. The following pilot plant run was operated 700 hours to approach steady state conditions and demonstrate sustainable operation.

The pilot plant reactor was a 10-gallon, glass-lined, jacketed, and agitated vessel operated with 8.5 gallons liquid fill. The first evaporator was sized to contain 3.3 gallons of liquid inventory in the bottom, and had a three-inch diameter by 38-inch height of packing. The second evaporator was sized to contain 0.17 gallons of liquid inventory, and had a two-inch diameter by 30-inch height of packing.

TABLE 1

Conditions of Dual Evaporator Experiments

| Process Condition or Result | Stream No. | Amount | Units |
|---|---|---|---|
| flow rates | | | |
| vinyl chloride | 01 | 1.7 | lb/hr |
| carbon tetrachloride | 02 | 5.3 | lb/hr |
| tributylphosphate | 03 | 0.029 | lb/hr |
| iron metal | 04 | 0.0047 | lb/hr |
| reactor effluent | 05 | 10.2 | lb/hr |
| catalyst recycle | 06 | 1.5 | lb/hr |

TABLE 1-continued

Conditions of Dual Evaporator Experiments

| Process Condition or Result | Stream No. | Amount | Units |
|---|---|---|---|
| 1st evap. overhead | 07 | 5.88 | lb/hr |
| 1st evap. bottoms | 08 | 4.32 | lb/hr |
| 2nd evap. overhead | 09 | 2.65 | lb/hr |
| catalyst purge | 10 | 0.186 | lb/hr |
| light ends recycle | 11 | 1.7 | lb/hr |
| products | 12 | 6.83 | lb/hr |
| temperatures and pressures | | | |
| reactor temperature | | 220 | F |
| reactor pressure | | 35 | psig |
| 1st flash twr. liquid temperature | | 187 | F |
| 1st flash twr. overhead pressure | | 20 | torr |
| 2nd flash twr. liquid temperature | | 207 | F |
| 2nd flash twr. overhead pressure | | 5 | torr |
| ratios | | | |
| HCC240f concentration in products | 12 | 83.5 | Wt % |
| purge ratio, lb purge/lb HCC240f in products | 10, 12 | 0.033 | lb/lb |
| HCC240f product recovery, yield on VnCl feed | 12, 01 | 96.9 | % |
| HCC240f purged, per lb of HjCC240f recovered in products | 10, 12 | 0.0046 | lb/lb |
| Hexachloropentane formed, moles per mole of HCC240f | | 0.018 | mol/mol |

A constant reactor liquid level was maintained by drawing a product stream from the reactor. This stream was fed into the first refluxed evaporator and distilled into distillate and bottom fractions. The first refluxed evaporator was equipped with a reboiler, a condenser, and a packed section irrigated with condensed distillate. Substantially all of the unconverted vinyl chloride and carbon tetrachloride contained in the reactor product stream was recovered in the distillate fraction. Most of the 1,1,1,3,3-pentachloropropane content in the reactor product stream was recovered in the distillate fraction. Substantially all of the hexachloropentane byproducts and all of the catalyst components remained in the bottom fraction. A constant liquid level was maintained in the first refluxed evaporator by drawing a bottom stream. This stream was fed into the second refluxed evaporator and separated into distillate and bottom fractions.

The second refluxed evaporator was equipped with a reboiler, a condenser, and a packed section irrigated with distillate. The second refluxed evaporator was smaller than the first and had only about one tenth the bottom liquid fill. Most of the 1,1,1,3,3-pentachloropropane contained in the bottoms of the first refluxed evaporator was recovered in the second unit's distillate fraction. Substantially all of the hexachloropentanes and heavy byproducts remained in the bottom fraction.

From Table 1, the total liquid flow from the bottom of the first evaporator was 4.32 lb/hr. The approximate density of this material was 12.9 lb/gallon, so that the volumetric flow rate was 0.335 gal/hr. Define the tower bottoms residence time as (liquid capacity of tower bottoms) (liquid flow rate from bottom of tower). Thus, the tower bottoms residence time for the first evaporator was 3.3 gallons (0.335 gal/hr= 9.9 hours. The total liquid flow from the bottom of the second evaporator was 0.19 lb/hr (purge) plus 1.5 lb/hr (catalyst recycle)=1.69 lb/hr. Since the density of this material is also approximately 12.9 lb/gal, the volumetric flow rate from the bottom of the tower was 0.131 gal/hr. Using the same formulation, the tower bottoms residence time for the second evaporator was therefore (0.17 gal)/(0.131 gal/hr)= 1.3 hour, or roughly 13% of the residence time in the first evaporator.

The purge/product ratio using two refluxed evaporators in series was 0.035 pounds bottom purge per pound of 1,1,1, 3,3-pentachloropropane recovered in combined distillate fractions. The 1,1,1,3,3-pentachloropropane concentration in the bottoms purge was 18 weight percent. This was is a substantial improvement over the best performance using a single flash tower.

Another surprising improvement was lower hexachloropentane selectivity. Until the second refluxed evaporator was installed in the pilot plant, the best sustainable hexachloropentane selectivity was 2.2 mole percent of 1,1,1,3,3-pentachloropropane selectivity. Hexachloropentane selectivity improved, decreasing to 1.8 mole percent selectivity using two refluxed evaporators.

Preferred Embodiment

Reactor(s)

The reaction generating 1,1,1,3,3-pentachloropropane from carbon tetrachloride and vinyl chloride is carried out in 1,1,1,3,3-pentachloropropane reactor(s). Preferably, the reactors are agitated, jacketed, pressure vessels constructed of corrosion resistant materials. Examples of these materials are Monel™, Hastelloy C-276, and glass lined steel. Reactor feeds are vinyl chloride, carbon tetrachloride, elemental iron, ferric chloride, TBP, recycled light ends, and recycled flash tower bottoms. Ferric chloride, elemental iron, and TBP are catalyst components. These components form Kharasch catalyst combinations and catalyze 1,1,1,3,3-pentachloropropane production from vinyl chloride and carbon tetrachloride. Side reactions form 1,1,1,3,5,5-hexachloropentane, 1,1,3,3,5,5-hexachloropentane, hexachloroethane and other minor byproducts.

Increasing the carbon tetrachloride to vinyl chloride concentration ratio decreases 1,1,3,3,5,5-hexachloropentane selectivity. Carbon tetrachloride is fed in excess to vinyl chloride. This makes vinyl chloride the reaction-limiting reagent. The preferred operating conditions cause greater than 90 percent vinyl chloride conversion. Excess carbon tetrachloride feed and substantially complete vinyl chloride conversion act together to increase the concentration ratio in the reaction media. Increasing ferric chloride concentration decreases 1,1,1,3,5,5-hexachloropentane selectivity. Ferric chloride is made in situ from elemental iron and is a component of recycled flash tower bottoms.

Reactor effluent composition, using preferred operating conditions, has the following composition ranges.
1. 0.2 to 2.0 weight percent vinyl chloride, most preferably 0.3 to 0.8 weight percent.
2. 10 to 50 weight percent carbon tetrachloride, most preferably 20 to 35 weight percent.
3. Less 3.0 weight percent light byproducts
4. 40 to 70 weight percent 1,1,1,3,3-pentachloropropane, most preferably 45 to 65 weight percent.
5. 1.0 to 8.0 weight percent 1,1,1,3,5,5-hexachloropentane, most preferably 2.0 to 5.0 weight percent
6. 2.0 to 12.0 weight percent 1,1,3,3,5,5-hexachloropentane, most preferably 3.0 to 6.0 weight percent
7. 0.5 to 3.0 weight percent ferric chloride, most preferably 0.7 to 1.7 weight percent
8. 2.0 to 9.0 weight percent tributylphosphate, most preferably 3.0 to 6.0 weight percent First Refluxed Evaporator The first refluxed evaporator's primary function is to separate more than ⅔ of the 1,1,1,3,3-pentachloropropane and substantially all of the lower boiling components from the catalyst components and hexachloropentanes while avoiding serious degradation of catalyst components. This is accomplished by operating the tower at low temperature, at low tower bottoms liquid residence time and at low catalyst concentration.

The first refluxed evaporator has a refluxed packed section. The packed section improves separation efficiency and prevents ferric chloride carryover.

Preferred operating conditions and results are:
1. 10 to 50 Torr bottom vapor pressure, most preferably 20 to 30 Torr
2. 160 to 240° F. bottom temperature, most preferably 190 to 200° F.
3. 5 to 95 percent HCC240f recovery in the distillate fraction, preferably 50 to 90 percent.
4. Tower bottoms liquid residence time of less than 5 days, preferably less that 24 hours.
5. Greater than 95 percent recovery of hexachloropentane isomers in the bottom fraction are preferably greater than 98 percent.
6. Less than 10 ppm ferric chloride concentration in the distillate fraction
7. Less than 50 ppm TBP in the distillate fraction Second Refluxed Evaporator The second refluxed evaporator's primary functions are to finish the separation of 1,1,1,3,3-pentachloropropane from hexachloropentanes and catalyst components and produce a concentrated stream containing the catalyst components in a form suitable for efficient recycle to the reactor. This is accomplished by operating the tower at very short residence time and at a moderate temperature. Preferred operating conditions and results are:
1. 3.0 to 15 Torr bottom vapor pressure, most preferably 4.0 to 8.0 Torr
2. 180 to 260° F. bottom temperature, most preferably 190 to 215° F.
3. Greater than 70 percent HCC240f recovery in the distillate fraction
4. Tower bottoms residence time of less than 12 hours, preferably less than 6 hours
5. Less than 10 ppm ferric chloride concentration in the distillate fraction
6. Less than 20 percent 1,1,1,3,3-pentachloropropane concentration in the bottom fraction, most preferably between 10 and 15 percent.

Most of the bottom fraction from the second flash tower is recycled to the HCC240f-reactor. A minor fraction of the second flash tower bottoms is purged to control heavy byproduct and inert catalyst accumulation.

Distillation

The distillate fractions of both refluxed evaporators are combined and further distilled to recover purified HCC240f. The combined distillate of both refluxed evaporators is fed to the first of two distillation steps. While it is possible to perform heavy byproduct separation in the first distillation, it is preferable to perform a light byproduct separation first.

Light byproducts, unconverted carbon tetrachloride, and unconverted vinyl chloride are collected in the distillate fraction from the light byproduct separation. Most of the light distillate fraction, and preferably 80 to 90 percent, is recycled to the reactor. A portion of the light distillate is purged to control light byproduct accumulation. The bottom fraction resulting from light byproduct distillation will contain 1,1,1,3,3-pentachloropropane and heavy byproducts. This bottom fraction is fed to the heavy byproduct distillation step. The heavy byproduct distillation step recovers highly purified 1,1,1,3,3-pentachloropropane product in the distillate fraction. 1,1,1,2,3-Pentachloropropane (HCC240db), which is an undesired isomer of HCC240f, and high-boiling byproducts are recovered in the bottom fraction. Under preferred conditions, HCC240db is the main component of the bottom fraction of the heavy byproduct distillation step.

Description of Alternative Embodiments

One alternative embodiment of the invention has in mind a further reduction of the cost of disposal of waste materials generated. The bottoms liquid from the both of the towers comprising the catalyst recovery system obviously contaminated with catalyst components and catalyst degradation products. The presence of these materials makes disposal of the small purge stream relatively expensive. In this alternative embodiment, the catalyst components are further concentrated by removing more of the volatile materials overhead in the second refluxed evaporator. This reduces the amount of catalyst-contaminated purge material from the second evaporator, but transfers a troublesome amount of hexachloropentane byproducts into the overhead of the second evaporator. Therefore, a new, small distillation tower must be installed to split the overhead from the second evaporator into relatively pure HCC240f overhead and relatively concentrated hexachloropentanes in the bottoms. The bottoms from this new tower does not contain catalyst components, and therefore can be disposed of more cheaply, or could even potentially be employed for other uses. The other major benefit of this procedure is that significantly more of the desired HCC240f is recovered.

Preferred operating conditions and results are:
1. Operation of the first refluxed evaporator of the catalyst recovery unit is similar to that of the preferred embodiment, above.
2. The pressure of the second refluxed evaporator is 3.0 to 15 Torr preferably 3.0 to 8.0 Torr.
3. The temperature of the second refluxed evaporator is 180 to 260 F. preferably 180 to 240 F.
4. Greater than 98% recovery of the fed HCC240f, and up to 67% recovery of the fed hexachloropentanes, in the distillate from the second refluxed evaporator.
5. Less than 10 ppm ferric chloride concentration in the distillate fraction from the second refluxed evaporator.
6. A relatively highly concentrated solution of catalyst components is produced in the bottom of the second refluxed evaporator, and this solution is suitable for catalyst recycle to the reactor.

7. Operation of the new, small tower designed to split the distillate fraction from the second refluxed evaporator into a new overhead material containing better than 98% purity HCC240f, and a new bottoms material containing less than 20 wt % HCC240f, being mainly hexachloropentanes. The new overhead material would be forwarded to the light byproducts separation step of the plant, and the new bottoms material could be disposed or used elsewhere.

In still other embodiments of the invention, a different Kharasch process product is produced instead of HCC240f. While not wishing to be limited by examples, such alternative products include 1,1,1,3-tetrachloropropane, made by the reaction of carbon tetrachloride and ethylene, or 1,1,1,3,3,3-hexachloropropane, made by the reaction of carbon tetrachloride with 1,1-dichloroethene.

Benefits and advantages of the disclosed invention are:

1) A much more highly concentrated catalyst recycle stream.

2) The recovery of a significantly higher percentage of 1,1,1,3,3-pentachloropropane.

3) Greater efficiency in the use of equipment.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A process for preparing a desired haloalkane comprising:
   (a) contacting a haloalkene feedstock and a haloalkane feedstock in the presence of effective amounts of catalyst components, ferrous chloride, ferric chloride, and a trialkylphosphate compound, under conditions effective to promote an addition reaction and to form a product stream containing said haloalkane product, higher boiling haloalkane by-products, unreacted feedstocks, and catalyst components, and
   (b) separating the desired haloalkane product from the high-boiling undesired haloalkane byproducts and the catalyst components using a two-stage catalyst recovery unit (CRU), wherein
      i. the bottom fraction from the first stage flows into the second stage, and the overhead fractions from the two stages are combined for further purification steps, and,
      ii. the first stage of the CRU recovers, in the distillate, between 50 and 90% of the desired haloalkane product contained in the reactor effluent, leaving more than 98% of the high-boiling undesired haloalkane byproducts in the bottom fraction, and,
      iii. the second stage of the CRU recovers, in the distillate, more than 70% of the remaining desired haloalkane product, leaving more than 33% of the high-boiling undesired haloalkane byproducts in the bottom fraction, together with the catalyst components, and
   (c) recycling most of the bottom fraction from the second stage of the CRU to the reactor, and purging a small fraction of it from the system to control byproduct concentrations in the reactor and to avoid excessive catalyst degradation.

2. The process of claim 1, wherein the first stage of the CRU roughly distills the desired haloalkane product and lower boiling components from the undesired high boiling haloalkane byproducts, higher boiling components, and catalyst components, producing a bottom fraction containing between 35 and 75 percent of the desired haloalkane product and wherein the second stage further separates the bottoms stream from the first stage into an overhead stream containing the desired haloalkane product and less than 2 wt. percent of the undesired high-boiling haloalkane byproducts, and produces a bottoms catalyst fraction suitable for recycle to the reactor, which contains less than 25 wt. percent of the desired haloalkane product.

3. The process of claim 1, wherein the first stage of the CRU is operated at 10 to 50 Torr bottom pressure, and at 160–240 degrees F. bottom temperature, and the liquid residence time, defined as the ratio of the volume of liquid contained in the bottom of the tower to the volumetric liquid flow rate from the bottom of the tower, is less than five days, and the second stage of the CRU is operated at 1 to 15 Torr bottom pressure, and at 180–260 degrees F. bottom temperature, and the liquid residence time is less than 12 hours.

4. The process of claim 1, wherein the first stage of the CRU is operated at less than 215 F. bottom temperature, and at less than five days liquid residence time, and the second stage of the CRU is operated at less than 240 F. bottom temperature, and at less than 12 hours liquid residence time.

5. The process of claim 1, wherein the first stage of the CRU is operated at 10 to 50 Torr bottom pressure, and at 160–240 F. bottom temperature.

6. The process of claim 1, wherein the second stage of the CRU is operated at 3 to 15 Torr bottom pressure and at 180–260 F. bottom temperature.

7. The process of claim 1, wherein the first stage of the CRU is operated at less than 215 F. bottom temperature.

8. The process of claim 1, wherein the second stage of the CRU is operated at less than 240 F. bottom temperature.

9. The process of Clam 1, wherein the liquid residence time in the first stage is less than five days and the liquid residence time in the second stage is less than 12 hours.

10. The process of claim 1, wherein the liquid residence time in the first stage is less than 24 hours and the liquid residence time in the second stage is less than 6 hours.

11. The process of claim 1, wherein the liquid residence time in the second stage is no more than 20% of the liquid residence time of the first stage, and the temperature of the second stage bottom liquid is no more than 25 degrees F. hotter than the temperature of the first stage bottom liquid.

12. The process of claim 1, wherein the desired haloalkane product is 1,1,1,3,3-pentachloropropane, the haloalkene feedstock is vinyl chloride, the haloalkane feed stock is tetrachloromethane, the main undesired high-boiling haloalkane byproducts are 1,1,1,3,5,5-hexachloropentane and 1,1,3,3,5,5-hexachloropentane, and the trialkylphasphate compound is tributylphosphate.

13. A method for generating 1,1,1,3,3-pentachloropropane comprising
   (a) reacting carbon tetrachloride with vinyl chloride in the presence of a catalyst comprising elemental iron, ferric chloride, and tributylphosphate, producing a reactor effluent, and
   (b) distilling the reactor effluent, separating 1,1,1,3,3-pentachloropropane and lower boiling components from high boiling components at a temperature and pressure which do not substantially inactivate the catalyst, and producing a bottom fraction containing the catalyst components and less than 50% of the 1,1,1,3,3-pentachloropropane contained in the reactor affluent from step (a), and (c) distilling the bottom fraction from step (b) to recover overhead at least 70% of the 1,1,1,3,3-pentachloropropane remaining in the bottom fraction from step (b), and producing a new bottom fraction suitable for recycle to the reactor, and (d) combining the distillate fractions of steps (b) and (c) for further purification of the 1,1,1,3,3-pentachloropropane product.

14. The method of claim 13, wherein the purified halohydrocarbon recovered is 1,1,1,3,3-pentachloropropane, and the olefin fed is vinyl chloride.

15. The method of claim 14, wherein the first refluxed evaporator is operated at about 10 to 50 Torr, with a bottom temperature of about 160 to 240 F., and the second refluxed evaporator is operated at about 1 to 15 Torr, with a bottom temperature of about 180–260 F.

16. The method of claim 15, wherein the liquid residence time in the first refluxed evaporator is less than 24 hours and the liquid residence time in the second refluxed evaporator is less than about six hours.

17. The method of claim 15, wherein the first refluxed evaporator has a pressure of about 20 Torr and a temperature of about 187 F., and the second refluxed evaporator has a pressure of about 5 Torr, and a temperature of about 207 F.

18. A process for preparing a desired haloalkane product comprising:

(a) contacting a haloalkene and a haloalkane feedstock in the presence of effective amounts of catalyst components ferrous chloride, ferric chloride, and a trialkylphosphate compound, under conditions effective to promote an addition reaction and to form a reactor effluent containing said haloalkane product, higher boiling haloalkane byproducts, unreacted feedstocks, and catalyst components, and (b) separating the desired haloalkane product from the high-boiling undesired haloalkane byproducts and the catalyst components using a two-stage catalyst recovery unit, wherein (i) the bottom fraction from the first stage flows into the second stage, and (ii) the first stage of the CRU recovers, in the distillate, between 50 and 90% of the desired haloalkane product contained in the reactor effluent, leaving more than 98% of the high-boiling undesired haloalkane byproducts in the bottom fraction, and (iii) the second stage of the CRU recovers, in the distillate, more than 70% of the remaining desired haloalkane product, leaving more than 33% of the high-boiling undesired haloalkane byproducts in the bottom fraction, together with the catalyst components, and (iv) further distilling the overhead fraction from step iii. to produce a new overhead fraction containing the desired haloalkane product and less than 1 wt. % of the high-boiling undesired haloalkane products and a new bottom fraction containing the undesired haloalkane product, and (v) disposing or otherwise using the bottom fraction of step iv., and (c) combining the overhead fraction of step iv. with the overhead frction of step ii. for further purification, and (d) recycling most of the bottom fraction from step iii. to the reactor, and purging a small fraction of it from the system to control byproduct concentrations in the reactor and to avoid excessive catalyst degradation.

\* \* \* \* \*